United States Patent
Shibata et al.

(10) Patent No.: US 11,155,797 B2
(45) Date of Patent: Oct. 26, 2021

(54) METHOD FOR PRODUCING PROTEIN

(71) Applicant: Kao Corporation, Tokyo (JP)

(72) Inventors: Nozomu Shibata, Wakayama (JP); Toshiharu Arai, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 17/251,963

(22) PCT Filed: Jun. 27, 2019

(86) PCT No.: PCT/JP2019/025547
§ 371 (c)(1),
(2) Date: Dec. 14, 2020

(87) PCT Pub. No.: WO2020/008987
PCT Pub. Date: Jan. 9, 2020

(65) Prior Publication Data
US 2021/0261933 A1    Aug. 26, 2021

(30) Foreign Application Priority Data

Jul. 4, 2018 (JP) ............... JP2018-127519
Nov. 9, 2018 (JP) ............... JP2018-211690

(51) Int. Cl.
*C12N 1/20* (2006.01)
*C12N 9/24* (2006.01)

(52) U.S. Cl.
CPC .... *C12N 9/2402* (2013.01); *C12Y 302/01004* (2013.01)

(58) Field of Classification Search
CPC ................................. C12N 9/2428
See application file for complete search history.

(56) References Cited

U.S. PATENT DOCUMENTS

| 6,326,477 | B1 | 12/2001 | Ilmén et al. |
| 2008/0199908 | A1 | 8/2008 | Smith et al. |
| 2015/0140615 | A1 | 5/2015 | Park et al. |
| 2018/0216121 | A1 | 8/2018 | Arai et al. |

FOREIGN PATENT DOCUMENTS

| CN | 101967501 A | 2/2011 |
| JP | H11-512930 A | 11/1999 |
| JP | 2015-039349 A | 3/2015 |
| JP | 2015-517319 A | 6/2015 |
| WO | WO 2017/018471 A1 | 2/2017 |

OTHER PUBLICATIONS

International Search Report for PCT/JP2019/025547; I.A. fd Jun. 27, 2019, dated Sep. 24, 2019 from the Japan Patent Office, Tokyo, Japan.

International Preliminary Report on Patentability (IPRP), Chapter I of the Patent Cooperation Treaty, including the Written Opinion, for PCT/JP2019/025547; I.A. fd Jun. 27, 2019, dated Jan. 5, 2021, by the International Bureau of WIPO, Geneva, Switzerland.

Ilmén M, et al., "Regulation of cellulase gene expression in the filamentous fungus *Trichoderma reesei*." Appl Environ Microbiol. Apr. 1997;63(4):1298-306. doi: 10.1128/AEM.63.4.1298-1306. 1997. PMID: 9097427; PMCID: PMC168424.

Amore A, et al., "Regulation of cellulase and hemicellulase gene expression in fungi." Curr Genomics. Jun. 2013;14(4):230-49. doi: 10.2174/1389202911314040002. PMID: 24294104; PMCID: PMC3731814.

Hermann T, "Industrial production of amino acids by coryneform bacteria." J Biotechnol. Sep. 4, 2003; 104(1-3):155-72. doi: 10.1016/s0168-1656(03)00149-4. PMID: 12948636.

Tian Y. et al., "pH Value Feedback Controlling of Carbon and Nitrogen Source Feeding in Lysine Fermentation," The Chinese Journal of Process Engineering 11(2): 402-406 (2011).

Nakazawa H., et al., Construction of a recombinant *Trichoderma reesei* strain expressing *Aspergillus aculeatus* β-glucosidase 1 for efficient biomass conversion. Biotechnol Bioeng. Jan. 2012;109(1):92-9. doi: 10.1002/bit.23296. Epub Sep. 2, 2011, PMID: 21830204.

Donzelli BG, et al., Interaction of ammonium, glucose, and chitin regulates the expression of cell wall-degrading enzymes in *Trichoderma atroviride* strain P1. Appl Environ Microbiol. Dec. 2001;67(12):5643-7. doi: 10.1128/AEM.67.12.5643-5647.2001. PMID: 11722918; PMCID: PMC93355.

*Primary Examiner* — Tekchand Saidha
(74) *Attorney, Agent, or Firm* — Sterne, Kessler, Goldstein & Fox P.L.L.C.

(57) ABSTRACT

Provided is an inexpensive and efficient microbiological method for producing a protein. The method for producing a protein comprises culturing a microorganism while feeding a mixture of glucose and ammonia.

16 Claims, 4 Drawing Sheets
Specification includes a Sequence Listing.

[FIG. 1]
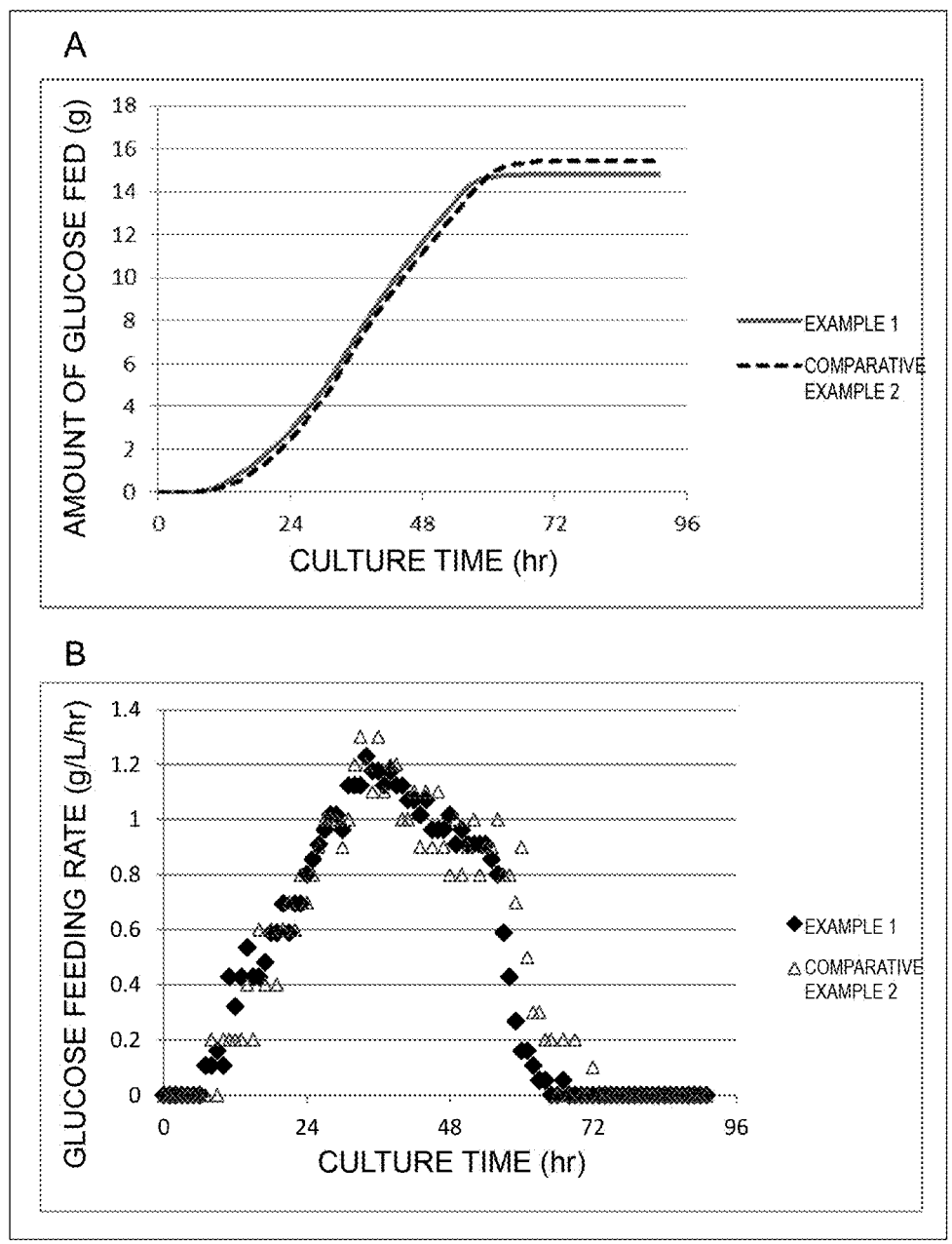

[FIG. 2]
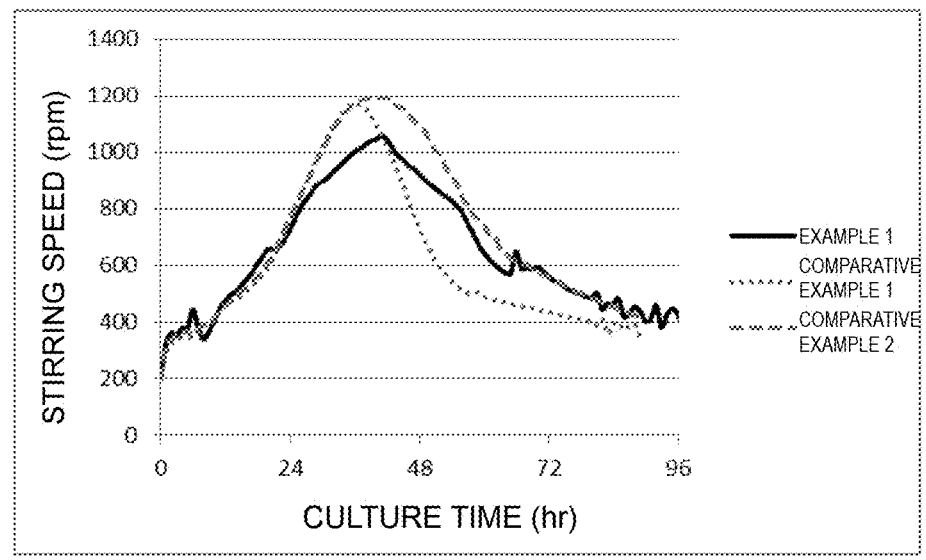
[FIG. 3]
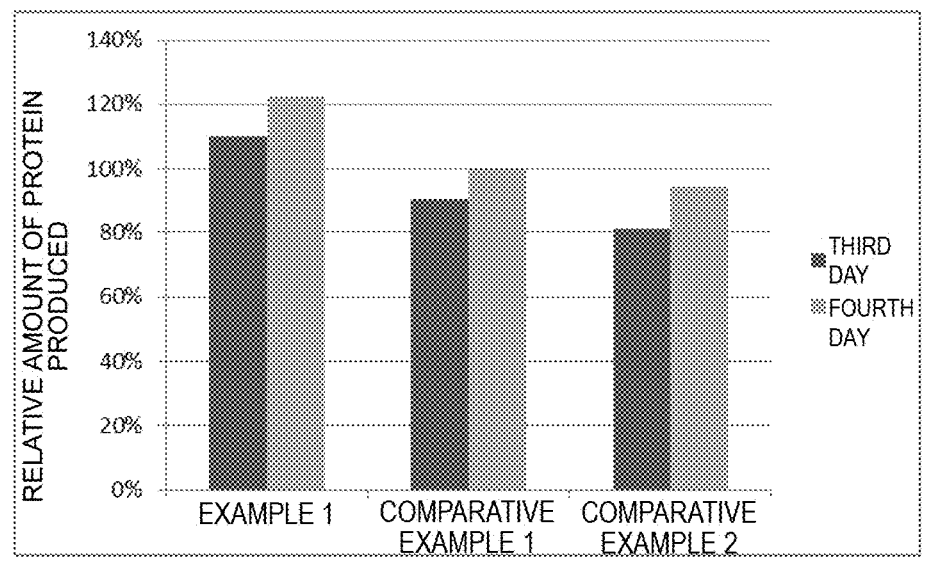

[FIG. 4]
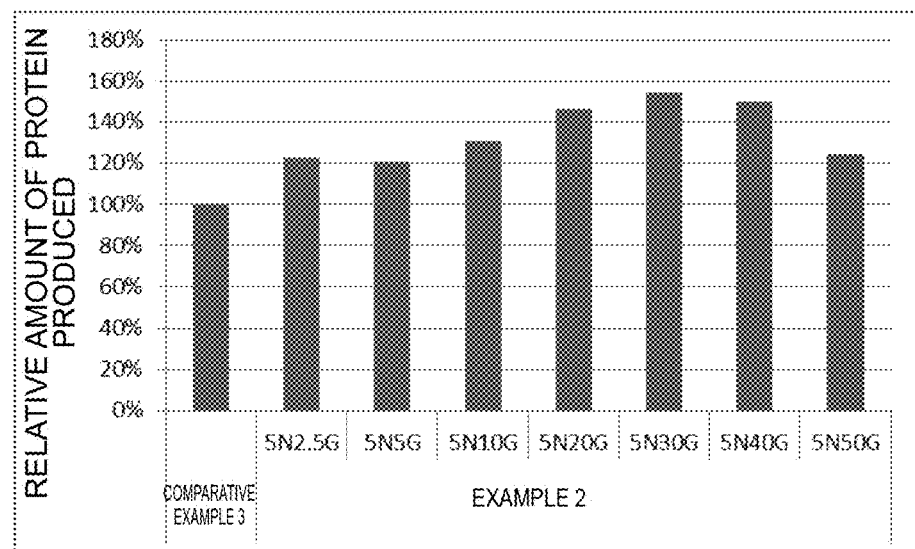
[FIG. 5]
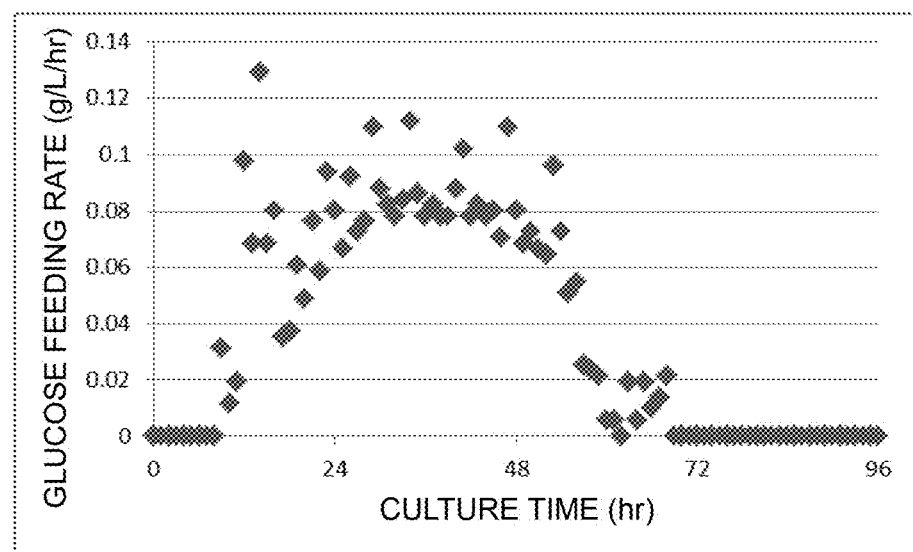

[FIG. 6]
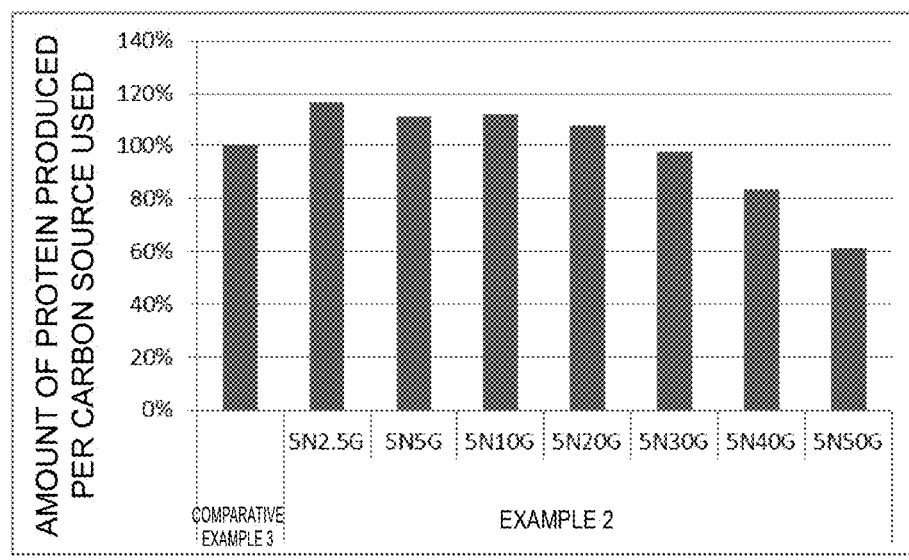

METHOD FOR PRODUCING PROTEIN

FIELD OF THE INVENTION

The present invention relates to a method for producing a protein using a microorganism.

BACKGROUND OF THE INVENTION

Filamentous fungi produce various cellulases and xylanases, and draw attention as plant polysaccharide-degrading fungi. In particular, *Trichoderma* is capable of producing a cellulase and xylanase at a time in large amounts, and is being studied as a microorganism for producing a cellulase-based biomass-degrading enzyme.

In culture of microorganisms, glucose has been heretofore commonly used as a carbon source. However, when glucose is present, a control mechanism called catabolite repression causes reduction or saturation of substance productivity of microorganisms. Wide domain transcription factors CreA, CreB, CreC, CreD and the like have been reported to be involved in catabolite repression of filamentous fungi such as *Aspergillus* (Patent Literature 1). It may be possible to regulate catabolite repression of *Aspergillus* by control of these transcription factors, but adequate results have not been obtained yet. For *Trichoderma*, analysis of the mechanism of catabolite repression has been proceeding (Patent Literature 2 and Non Patent Literature 1). However, much of the mechanism of catabolite repression of *Trichoderma* is still unclear, and avoidance of repression has not been achieved.

Production of protein such as an enzyme by a microorganism may require an inducing substance in addition to carbon sources. For example, expression of an alpha-amylase gene of *Aspergillus oryzae* is induced by starch, maltose and the like. Expression of main cellulase genes cbh1, cbh2, egl1 and egl2 of *Trichoderma* is induced by cellulose, cellobiose and the like (Non Patent Literature 2). Starch, maltose, cellulose and cellobiose can also be used as carbon sources for culturing. In production of cellulase using a microorganism, microcrystalline cellulose such as Avicel is generally used.

Patent Literature 3 discloses a method for producing a cellulase by a microorganism using lignocellulose instead of pure cellulose as an inducing substance. In Patent Literature 3, a cellulase is produced by culturing *Trichoderma* with glucose fed as a carbon source and phosphoric acid or ammonia water fed as a pH adjuster in a culture medium containing a cellulose-based material. Non-Patent Literature 3 discloses that an amino acid was produced by *Corynebacterium* with saccharides repeatedly or continuously fed to a culture medium. Patent Literature 4 and Non Patent Literature 4 disclose that lysine was fermentatively produced by feeding a mixed solution of glucose and ammonia to a culture, and adding a carbon source and a nitrogen source while controlling the pH value, and that this method increased the productivity of lysine.

[Patent Literature 1] JP-A-2015-39349
[Patent Literature 2] JP-A-11-512930
[Patent Literature 3] US 2008/0199908A
[Patent Literature 4] CN 101967501C
[Non Patent Literature 1] Appl. Environ. Microbiol., 63: 1298-1306 (1997)
[Non Patent Literature 2] Curr. Genomics, 14: 230-249 (2013)
[Non Patent Literature 3] Journal of Biotechnology, 104: 155-172 (2003)
[Non Patent Literature 4] The Chinese Journal of Process Engineering, 11(3): 492-496 (2011)

SUMMARY OF THE INVENTION

The present invention provides a method for producing a protein, comprising culturing a microorganism while feeding a mixture of glucose and ammonia.

BRIEF DESCRIPTION OF THE DRAWINGS

FIG. 1 shows a cumulative amount (A) and an hourly amount (B) of glucose fed to a culture in each of Example 1 and Comparative Example 2.

FIG. 2 shows a time-dependent change in stirring rate during culture in each of Example 1 and Comparative Examples 1 and 2.

FIG. 3 shows a relative amount of protein produced in each of Example 1 and Comparative Examples 1 and 2. Each value is a relative value against the amount of protein produced on day 4 of culture in Comparative Example 1, which is defined as 100%.

FIG. 4 shows a relative amount of protein produced in each of Example 2 and Comparative Example 3. Each value is a relative value against the amount of protein produced in Comparative Example 3, which is defined as 100%.

FIG. 5 shows an hourly amount of glucose fed to a culture cultured using a 5% ammonia/2.5% glucose aqueous solution in Example 2.

FIG. 6 shows a relative amount of protein produced per carbon source used in each of Example 2 and Comparative Example 3. Each value is a relative value against the amount of protein produced in Comparative Example 3, which is defined as 100%.

DETAILED DESCRIPTION OF THE INVENTION

All patent documents, non-patent documents and other publications cited herein are incorporated herein by reference in their entirety.

As used herein, the "upstream" and the "downstream" with respect to a gene means upstream and downstream in a transcription direction of the gene. For example, the "gene located downstream of a promoter" means that the gene is present on the 3' side of the promoter in a DNA sense strand, and the upstream of the gene means a region on the 5' side of the gene in the DNA sense strand.

As used herein, the "operable linkage" between a promoter and a gene means that the promoter and the gene are linked in such a manner that the promoter can induce transcription of the gene. The procedure for "operable linkage" between a promoter and a gene is well known to persons skilled in the art.

As used herein, the "promoter activity" means activity of promoting expression of a gene located downstream of the promoter, more specifically activity of promoting transfer of a gene located downstream of the promoter from DNA to mRNA.

As used herein, the term "intrinsic" which is used in connection with functions, properties and traits of cells is used to indicate that the functions, properties and traits are inherent in the cells. In contrast, the term "foreign" is used to indicate functions, properties and traits which are not inherent in the cells, but are introduced from the outside. For example, the "foreign" gene or polynucleotide is a gene or polynucleotide introduced into cells from the outside. The foreign gene or polynucleotide may be one derived from an organism identical in species to cells into which the foreign gene or polynucleotide has been introduced, or one derived from an organism different in species from the cells (i.e., a heterologous gene or polynucleotide)

As used herein, the "identity of at least 90%" in connection with an amino acid sequence or a nucleotide sequence means an identity of 90% or more, preferably 95% or more, more preferably 96% or more, even more preferably 97% or more, even more preferably 98% or more, even more preferably 99% or more.

As used herein, the identity of a nucleotide sequence and an amino acid sequence is calculated by the Lipman-Pearson method (Science, 1985, 227: 1435-1441). Specifically, the identity is calculated by performing analysis with a unit size to compare (ktup) of 2 by using the homology analysis (Search homology) program of gene information processing software Genetyx-Win.

Development of an inexpensive and efficient culture technique for producing a protein such as an enzyme by a microorganism is required. By fed-batch culture in which glucose is repeatedly or continuously fed to a culture, catabolite repression may be suppressed to improve the productivity of protein by a microorganism. However, it has been predicted that in production of protein by fed-batch culture, precise control of the glucose concentration in a culture is essential because the protein synthesis process does not sufficiently proceed when the amount of glucose is small, and on the other hand, feeding of a large amount of glucose causes catabolite repression. Further, it has been predicted that since production of protein by fed-batch culture requires feeding of a nitrogen source in addition to glucose, it is necessary to install respective feeding lines to control the concentrations of glucose and nitrogen source.

The present inventors produced a protein such as an enzyme by mixing an ammonia aqueous solution, which is known to serve as a nitrogen source and a pH adjuster, with glucose in advance, and culturing a microorganism while feeding the resulting mixture. Resultantly, against the above-described prediction, it was found that a protein can be produced with a high yield without requiring precise control of the glucose concentration and with the use of only one feeding line. Further, unexpectedly, it was found that this method further improves the protein productivity as compared to a method in which an ammonia aqueous solution and glucose are separately fed.

According to the present invention, the protein productivity of a microorganism can be improved in a convenient procedure. The method of the present invention further improves the protein productivity as compared to a method in which an ammonia aqueous solution and glucose are separately fed. Further, the method of the present invention involves a small number of feeding lines, does not require precise control of feeding, and therefore reduces the amount of time and labor and the cost spent for culturing while improving the protein productivity as compared to a method in which an ammonia aqueous solution and glucose are separately fed.

The method for producing a protein according to the present invention comprises culturing a microorganism while feeding a mixture of glucose and ammonia.

The mixture of glucose and ammonia is a liquid mixture prepared by mixing glucose and ammonia. For example, the mixture is a mixture of glucose, ammonia and a solvent thereof (e.g. water). Preferably, the mixture is a mixture prepared by mixing glucose or an aqueous solution thereof, and ammonia, a salt thereof or an aqueous solution thereof, and water if necessary. More preferably, the mixture is a mixture obtained by mixing glucose, and an ammonia aqueous solution, and water if necessary. In preparation of the mixture of glucose and ammonia, glucose and ammonia may be mixed at a mass ratio of preferably from 0.5 to 10:1, more preferably from 2 to 8:1. When the ratio of glucose is excessively high, cells tend to make a transition from an enzyme-producing state to a growing state, leading to reduction of the enzyme productivity. On the other hand, when the ratio of glucose is excessively low, the amount of carbon source is insufficient, and resultantly, improvement in the enzyme productivity cannot be expected. In preparation of the mixture of glucose and ammonia, the amount of glucose added may be adjusted to preferably from 2 to 90 g, more preferably from 5 to 80 g per 100 mL of the resulting mixture. When the amount of glucose added to the mixture is excessively small, a large amount of the mixture is fed to the culture, so that culture equipment is overloaded. On the other hand, when the amount of glucose added to the mixture is excessively large, it is difficult to control the amount of the mixture fed to the culture. For example, the mixture may be prepared by mixing an appropriate amount of glucose and an ammonia aqueous solution so as to enable achievement of the above-described ratio of glucose to ammonia and/or amount of glucose added, or may be prepared by mixing an arbitrary amount of glucose and an ammonia aqueous solution, and then appropriately diluting the resulting mixture with water so as to enable achievement of the above-described ratio of glucose to ammonia and/or amount of glucose added.

The pH of the mixture of glucose and ammonia at 25° C. is preferably an alkaline pH, more preferably 8 or more, even more preferably 9 or more, even more preferably 10 or more, and preferably 13 or less. Preferably, the pH of the mixture is adjusted to be within the above-described range using a pH adjuster such as an alkaline agent if necessary. The pH of the mixture can be measured using a common pH meter. For example, a pH measuring composite electrode (e.g. Ground Glass Sleeve Type manufactured by HORIBA, Ltd.) connected to a pH meter (pH/Ion Meter F-52 manufactured by HORIBA Ltd.) is used. A saturated potassium chloride aqueous solution (3.33 mol/L) is used as a pH electrode internal liquid. The measurement is performed at 25° C. Preferably, the mixture of glucose and ammonia is used as a pH adjuster preferably for the culture.

The mixture of glucose and ammonia may further contain other substances which can be typically added to a microbial culture medium. The other substances are preferably substances which do not impair the pH adjustment function of the mixture, and examples thereof include organic salts, inorganic salts, other pH adjusters, carbon sources and nitrogen sources other than glucose and ammonia, surfactants, and defoaming agents.

In the method of the present invention, the mixture of glucose and ammonia is fed to a microbial culture. The amount of the mixture fed to the culture is preferably 8 g/hr or less, more preferably 6 g/hr or less, even more preferably from 0.05 to 8 g/hr, even more preferably from 0.1 to 6 g/hr per L of an initial culture medium (culture medium free from the mixture fed) in terms of the amount of glucose added to the mixture. When the amount of glucose fed is large, catabolite repression may occur. On the other hand, the amount of the (entire) mixture fed to the culture may be appropriately adjusted according to the content of glucose or ammonia, or the pH of the culture as described below, and is not particularly limited. From the viewpoint of economic efficiency, the amount of the (entire) mixture fed may be adjusted to about from 0.1 to 10 g/hr, preferably about from 0.3 to 8 g/hr per L of an initial culture medium.

Preferably, the pH of the culture is adjusted by feeding the mixture of glucose and ammonia in culture of a microorganism according to the method of the present invention. In this case, the amount of the mixture fed and the timing of feeding the mixture depend on the pH of the culture to which the mixture is fed. Suitably, an initial culture medium with a predetermined pH is prepared in a usual procedure, followed by culturing while the mixture of glucose and ammonia is fed in such a manner that the culture after being fed maintains the predetermined pH value. While it is preferable to use only the mixture of glucose and ammonia for adjustment of the pH of the culture during culture, another pH adjuster may be used in combination. Measurement of the pH of the culture and control of the amount fed based on the pH value can be performed using a commercially available jar fermenter or the like. The pH of the culture can be set to an appropriate value according to the species of organism, and the type of protein to be produced. For example, when the microorganism is filamentous fungi, the culture is maintained at a pH of preferably from 3 to 7, more preferably from 3.5 to 6. In general, the pH of the culture can be measured with an electrode provided in a jar fermenter. Suitably, the pH of the culture in the present invention is a value measured with a pH sensor such as F-635 Autoclavable pH Electrode (Broadley-James Corp) or 405-DPAS-SC-K8S pH sensor (ME TTLER TOLEDO) at a culture temperature of 28° C.

In the present invention, the initial culture medium used for culturing a microorganism (culture medium to which the mixture of glucose and ammonia has not been fed) may be a culture medium which is commonly used for culturing the microorganism. For example, the initial culture medium may contain various components which are generally contained in microbial culture media, such as carbon sources, nitrogen sources, metal salts such as magnesium salts and zinc salts, sulfates, phosphates, pH adjusters, surfactants and defoaming agents. The composition of components in the culture medium can be appropriately selected. The initial culture medium may be any of a synthetic culture medium, a natural culture medium and a semisynthetic culture medium, or may be a commercially available culture medium. The initial culture medium is preferably a liquid culture medium.

Preferably, a microorganism is cultured in the presence of a substance which induces expression of a gene encoding a target protein in the method of the present invention. This enables further enhancement of the productivity of target protein. More specifically, the microbial culture may contain the inducing substance. For example, the inducing substance may be contained in the initial culture medium, fed to the culture, or both contained and fed. Preferred examples of the inducing substance include cellulose and cellobiose, and one or both thereof can be used. Cellulose or cellobiose in the culture can be consumed as a carbon source while acting as an inducing substance. The concentration of cellulose or cellobiose in the culture is preferably from 1 to 15 mass/vol % as a total concentration of cellulose and cellobiose. For example, when cellulose or cellobiose is added to the initial culture medium, the concentration of cellulose or cellobiose in the initial culture medium is preferably from 1 to 15 mass/vol % as a total concentration of cellulose and cellobiose. It is known that expression of a cellulase gene of filamentous fungi such as *Trichoderma* is induced by cellulose, cellobiose or the like, and catabolite repression is caused by glucose (Patent Literature 2 and Non Patent Literatures 1 and 2). Therefore, the method of the present invention using the inducing substance can be suitably used for production of a cellulase using filamentous fungi.

Alternatively, a gene encoding a target protein is linked to a promoter which is induced by cellulose or cellobiose, such as a promoter of a gene encoding cellulase of filamentous fungi (so called cellulase gene promoter of filamentous fungi), whereby expression of a gene of the target protein can be induced by cellulose or cellobiose. Therefore, in a preferred embodiment of the method of the present invention, the microorganism is cultured in the presence of at least one selected from the group consisting of cellulose and cellobiose, the microorganism contains a promoter which is induced by cellulose or cellobiose, and a gene encoding a target protein is operably linked downstream of the promoter.

Examples of the promoter which is induced by cellulose or cellobiose include promoters of cellulase genes or xylanase genes of filamentous fungi. Examples of the promoters of cellulase genes of filamentous fungi include promoters of cellulase genes of *Trichoderma* fungi, and preferred examples thereof include promoters of cellulase genes of *Trichoderma reesei* which consist of a nucleotide sequence of SEQ ID NO: 1 or 2. Examples of the promoters of xylanase genes of filamentous fungi include promoters of xylanase genes of *Trichoderma* fungi, and preferred examples thereof include promoters of xylanase genes of *Trichoderma reesei* which have a nucleotide sequence of SEQ ID NO: 3. Further examples of the promoters which are induced by cellulose or cellobiose include polynucleotides consisting of a nucleotide sequence with an identity of at least 90% to any of the nucleotide sequences of SEQ ID NOS: 1 to 3 and having promoter activity induced by cellulose or cellobiose.

The promoter may be a promoter intrinsic to a microorganism cultured in the method of the present invention, or a foreign promoter introduced into the microorganism. Linkage of such a promoter to a gene encoding a target protein can be performed in accordance with a known procedure such as a restriction enzyme method or a homologous recombination method. For example, a vector or DNA fragment having a polynucleotide containing a gene encoding a target protein is introduced into microbial cells, and the polynucleotide is incorporated downstream of a target promoter in a genome, whereby the promoter and the gene encoding the target protein are operably linked on the genome. Alternatively, a vector or DNA fragment having a promoter sequence and a polynucleotide containing a gene encoding a target protein linked downstream of the promoter sequence may be constructed, and introduced into microbial cells. If necessary, the vector or DNA fragment may further have selection markers such as antibiotic resistance genes and auxotrophy-related genes.

The vector may be a vector capable of autonomously proliferating and replicating outside a chromosome such as a plasmid, or may be a vector which is incorporated in a chromosome. The preferred type of vector depends on the species of a microorganism into which the vector is introduced. Preferred examples of the vector for filamentous fungi include, but are not limited to, plasmids containing AMA1 which act as an autonomous replication factor in *Aspergillus* microorganisms.

For introduction of the vector or DNA fragment into a microorganism, a general transformation method can be used, such as an electroporation method, a transformation method, a transfection method, a conjugation method, a protoplast method, a particle gun method or an agrobacterium method.

A microorganism having a target vector or DNA fragment introduced therein can be selected by using a selection marker. For example, when the selection marker is an antibiotic resistance gene, a microorganism having a target vector or DNA fragment introduced therein can be selected by culturing the microorganism in a culture medium containing the antibiotic. For example, when the selection marker is an auxotrophy-related gene such as an amino acid synthesis-related gene or a base synthesis-related gene, the gene is introduced into a host having the auxotrophy, followed by using existence or non-existence of the auxotrophy as an index to thereby select a microorganism having a target vector or DNA fragment introduced therein. Alternatively, the DNA sequence of a microorganism can be examined by PCR or the like to confirm introduction of a target vector or DNA fragment.

The gene encoding a target protein, which is linked to the promoter, may be linked to a secretory signal peptide. Due to linkage to the secretory signal peptide, the expressed target protein is secreted to the outside of cells, and therefore the target protein can be isolated from the culture supernatant without destroying the microbial cells. Examples of the secretory signal peptide include signal peptides derived from cellobiohydrolase 1 of *Trichoderma reesei*, alpha-amylase of *Aspergillus oryzae*, glucoamylase of *Rhizopus oryzae* or alpha-factors of *Saccharomyces cerevisiae*.

Examples of the target protein produced by the method of the present invention include oxidoreductases, transferases, hydrolases, lyases, isomerases, ligases or synthetases, glycolytic enzymes, lactate synthetases (LDH etc.), tricarboxylic acid cycle (TCA) enzymes. The target protein may be protein intrinsic to a microorganism cultured by the method of the present invention, or may be foreign protein. Preferred examples of the target protein include enzymes involved in biomass degradation or biomass saccharification. Examples of the enzymes involved in biomass degradation or biomass saccharification include cellulases (e.g. β-endoglucanase, cellobiohydrolase and β-glucosidase), hemicellulases (e.g. endoxylanase, β-xylosidase, arabinofuranosidase, glucuronidase, acetylxylan esterase, mannanase, β-mannosidase and ferulic acid esterase), and xylanase. Of these, cellulases are preferable. The enzyme involved in biomass degradation or biomass saccharification is preferably an enzyme derived from filamentous fungi, more preferably an enzyme derived from *Trichoderma* fungi.

Examples of the microorganisms cultured in the method of the present invention include bacteria, yeasts and filamentous fungi. Of these, filamentous fungi are preferable. Examples of the filamentous fungi include *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Rhizopus, Schizophyllum, Talaromyces, Thermoascus, Thielavia, Tolypocladium, Trametes* and *Trichoderma*. Of these, *Acremonium, Aspergillus, Chrysosporium, Fusarium, Humicola, Myceliophthora, Neurospora, Penicillium, Piromyces, Talaromyces, Thermoascus, Thielavia* and *Trichoderma* are preferable, and *Trichoderma* is more preferable. As *Trichoderma* fungi, *Trichoderma reesei* and variants thereof are preferable. Examples of *Trichoderma reesei* and variants thereof include *Trichoderma reesei* QM9414 strain and variants thereof.

The conditions for culturing a microorganism in the present invention can be appropriately determined conventionally depending on the species of the microorganism and the scale of culture.

Subsequently, a target protein is collected from the culture. When the protein is secreted in the culture supernatant, the protein can be collected from the culture supernatant. When the protein is contained in cells, the cells are destroyed, and a fraction containing the protein is extracted, and used to collect the protein. The protein can be collected by a method which is commonly used in the field, such as decantation, membrane separation, centrifugation, electrodialysis, use of an ion-exchange resin, distillation, salting-out or a combination thereof. The collected target protein may be further isolated or purified.

When the target protein is secreted in the culture supernatant, the microorganism used for producing the protein in the present invention can be repeatedly used. That is, microbial cells separated from the culture supernatant are collected, seeded in the initial culture medium again, and cultured while a mixture of glucose and ammonia is fed, whereby the target protein can be produced again.

The method for producing protein according to the present invention may be a batch method in which culture of a microorganism is alternated with collection of protein accumulated in a culture and replacement of a culture medium, or a semibatch or continuous method in which culture of a microorganism and collection of protein are performed in parallel while the microorganism and a culture medium are partially replaced intermittently or continuously.

As illustrative embodiments of the present invention, the following substances, production methods, uses, methods and the like are disclosed herein. It is to be noted that the present invention is not limited to these embodiments.

[1] A method for producing a protein, comprising culturing a microorganism while feeding a mixture of glucose and ammonia.

[2] The method according to [1], wherein preferably, the culturing is performed in the presence of at least one selected from the group consisting of cellulose and cellobiose.

[3] The method according to [2], wherein preferably, the microorganism contains a cellulose-inducing promoter or a cellobiose-inducing promoter, and the promoter is
preferably a cellulase gene promoter of a filamentous fungus or a xylanase gene promoter of a filamentous fungus,
more preferably a cellulase gene promoter of a *Trichoderma* fungus or a xylanase gene promoter of a *Trichoderma* fungus.

[4] The method according to [3], wherein preferably, a gene encoding the protein is linked downstream of the promoter.

[5] The method according to [4], wherein preferably, the promoter is the cellulase gene promoter of a filamentous fungus, and the protein is an enzyme.

[6] The method according to [4] or [5], wherein preferably the protein is an enzyme, preferably an enzyme involved in biomass degradation or biomass saccharification, more preferably a cellulase, and the enzyme involved in biomass degradation or biomass saccharification is preferably an enzyme derived from a filamentous fungus, more preferably an enzyme derived from a *Trichoderma* fungus, even more preferably a filamentous fungus-derived cellulase, even more preferably a *Trichoderma* fungus-derived cellulase.

[7] The method according to any one of [1] to [6], wherein the mixture is fed in an amount of preferably 8 g/hr or less, more preferably 6 g/hr or less, even more preferably from 0.05 to 8 g/hr, even more preferably from 0.1 to 6 g/hr per L of an initial culture medium in terms of the amount of glucose added to the mixture.

[8] The method according to any one of [1] to [7], wherein by feeding the mixture, the pH of the culture is adjusted to preferably from 3 to 7, more preferably from 3.5 to 6.

[9] The method according to any one of [1] to [8], wherein the mixture contains glucose and ammonia at a mass ratio of preferably from 0.5 to 10:1, more preferably from 2 to 8:1.

[10] The method according to any one of [1] to [9], wherein preferably, the mixture contains glucose in an amount of from 2 to 90 g per 100 mL.

[11] The method according to any one of [1] to [10], wherein a pH of the mixture is preferably an alkaline pH, more preferably 8 or more, even more preferably 9 or more, even more preferably 10 or more, and preferably 13 or less at 25° C.

[12] The method according to any one of [1] to [11], wherein the microorganism is preferably a filamentous fungus.

[13] The method according to [12], wherein the filamentous fungus is preferably a *Trichoderma* fungus.

[14] The method according to [13], wherein the *Trichoderma* fungus is preferably *Trichoderma reesei*.

[15] The method according to any one of [2] to [12], wherein the microorganism is preferably a filamentous fungus, and the protein is preferably an enzyme involved in biomass degradation or biomass glycosylation, and more preferably a cellulase.

[16] The method according to [15], wherein the filamentous fungus is preferably a *Trichoderma* fungus.

[17] The method according to [16], wherein the *Trichoderma* fungus is preferably *Trichoderma reesei*.

[18] The method according to any one of [2] to [17], wherein a concentration of cellulose or cellobiose in a culture is preferably from 1 to 15 mass/vol % as a total concentration of cellulose and cellobiose.

[19] The method according to any one of [1] to [18], wherein preferably, the method further comprises collecting the protein from a culture of the microorganism.

[20] The method according to any one of [1] to [19], wherein preferably, the method comprises preparing the mixture of glucose and ammonia or a salt thereof, and feeding the prepared mixture to the culture medium.

EXAMPLES

Hereinafter, the present invention will be described in more detail on the basis of Examples, which should not be construed as limiting the present invention. In Examples below, "%" means "w/v %" unless otherwise specified. The pH of each of an ammonia aqueous solution and an ammonia/glucose aqueous solution was measured at 25° C. using a pH meter (pH/Ion Meter F-52 from HORIBA Ltd.) connected to a pH measuring composite electrode (Ground Glass Sleeve Type from HORIBA, Ltd.) [pH electrode internal liquid: saturated potassium chloride aqueous solution (3.33 mol/L)]. The pH of the culture was measured using a pH sensor of F-635 Autoclavable pH Electrode (Broadley-James Corp) or 405-DPAS-SC-K8S pH Sensor (METTLER TOLEDO) provided in a jar fermenter.

Example 1

*Trichoderma reesei* X3AB1 strain (J. Ind. Microbiol. Biotechnol., 2012, 174: 1-9; hereinafter, referred to as X3AB1 strain) was cultured in a cellulose-containing culture medium to produce a protein containing a cellulase. As preculture, 50 mL of a culture medium was added to a 500 mL flask, spores of X3AB1 strain were inoculated at $1 \times 10^5$ cells/mL, and shaking culture was performed at 220 rpm (PRXYg-98R from PRECI CO., LTD.) at 28° C. The culture medium composition was as follows: 1% glucose, 0.14% $(NH_4)_2SO_4$, 0.2% $KH_2PO_4$, 0.03% $CaCl_2.2H_2O$, 0.03% $MgSO_4.7H_2O$, 0.1% Bacto Peptone (BD Difco), 0.05% Bacto Yeast extract (BD Difco), 0.1% Tween 80, 0.1% Trace element and 50 mM tartrate buffer (pH 4.0). The composition of the Trace element was as follows: 6 mg of $H_3BO_3$, 26 mg of $(NH_4)_6Mo_7O_{24}.4H_2O$, 100 mg of $FeCl_3.6H_2O$, 40 mg of $CuSO_4.5H_2O$, 8 mg of $MnCl_2.4H_2O$ and 200 mg of $ZnCl_2$ which were diluted to 100 mL with distilled water.

Main culture was performed after 2 days of preculture. The initial culture medium in the main culture contained 10% powder cellulose (KC FLOCK W100 from Nippon Paper Industries Co., Ltd.), and other culture medium components: 0.42% $(NH_4)_2SO_4$, 0.2% $KH_2PO_4$, 0.03% $CaCl_2.2H_2O$, 0.03% $MgSO_4.7H_2O$, 0.1% Bacto Peptone, 0.05% Bacto Yeast extract, 0.1% Tween 80, 0.1% Trace element and 0.2% Antifoam PE-L. A preculture solution was inoculated in an amount of 10% (v/v %) in a 1 L-volume jar fermenter BMZ-01KP2 (Biott) containing 500 mL of the medium, and culture was performed for 4 days. The jar fermenter was set as follows: temperature: 28° C., aeration rate: 0.5 vvm, pH: 4.5±0.1, and stirring rate: varied so as to maintain DO=3.0 ppm. Glucose was dissolved in a 10% ammonia aqueous solution, and the solution was appropriately diluted to prepare a mixture of glucose and ammonia (hereinafter, referred to as a 5% ammonia/20% glucose aqueous solution). During culture, the 5% ammonia/20% glucose aqueous solution (pH 11.3) was appropriately fed to the culture solution. The amount of the 5% ammonia/20% glucose aqueous solution fed was controlled so that the pH of the culture solution was maintained within the above-described predetermined range.

Comparative Example 1

A microorganism was cultured in the same manner as in Example 1 except that instead of the 5% ammonia/20% glucose aqueous solution, a 5% ammonia aqueous solution (pH 12.3) was fed.

Comparative Example 2

A microorganism was cultured in the same manner as in Example 1 except that instead of the 5% ammonia/20% glucose aqueous solution, a 10% ammonia aqueous solution (pH 12.7) was used for pH adjustment, and a 40% glucose aqueous solution was fed from another feeding line under conditions shown in Table 1.

TABLE 1

| Culture time (hr) | Fed amount (g/L Initial culture medium/hr) |
|---|---|
| 0-6 | 0 |
| 6-9 | 0.05 |
| 9-12 | 0.1 |
| 12-15 | 0.15 |
| 15-20 | 0.25 |
| 20-22 | 0.3 |
| 22-25 | 0.4 |

TABLE 1-continued

| Culture time (hr) | Fed amount (g/L Initial culture medium/hr) |
|---|---|
| 25-27 | 0.45 |
| 27-31 | 0.5 |
| 31-39 | 0.6 |
| 39-46 | 0.5 |
| 46-56 | 0.45 |
| 56-60 | 0.4 |
| 60-61 | 0.3 |
| 61-62 | 0.15 |
| 62-65 | 0.1 |
| 65-69 | 0.05 |

Test 1: Amount of Glucose Fed

The weights of the 5% ammonia/20% glucose aqueous solution (pH 11.3) and the 40% glucose aqueous solution fed to the culture solution in each of Example 1 and Comparative Example 2 were monitored with an electronic balance. The weight of glucose fed to the culture solution was calculated from the content of glucose contained in the aqueous solution and the specific gravity of the aqueous solution. FIG. 1A shows a cumulative amount of glucose fed to the culture solution and FIG. 1B shows a time-dependent change in the hourly amount of glucose fed to the culture solution in each of Example 1 and Comparative Example 2. The cumulative amounts as well as the hourly amounts of glucose fed in Example 1 and Comparative Example 2 followed substantially the same curve.

Test 2: Stirring Behavior

FIG. 2 shows a time-dependent change in stirring rate of the jar fermenter in each of Example 1 and Comparative Examples 1 and 2. Since the stirring rate is set to vary so that DO=3.0 ppm is maintained, a change in stirring rate substantially corresponds to a change in oxygen demand during culture. As compared to Comparative Example 1, the stirring rate tended to increase in Comparative Example 2, and the stirring rate tended to decrease in Example 1. This fact indicated that when the mixture of glucose and ammonia was fed, some phenomenon occurred which caused a decrease in stirring rate (oxygen demand) as compared to a case where glucose and ammonia were separately fed.

Test 3: Amount of Protein Produced

The culture solutions obtained in Example 1 and Comparative Examples 1 and 2 were centrifuged. Subsequently, fungal cells were separated from the supernatant with a membrane filter 25CS020AN (Advantech). The concentration of protein in the supernatant was measured by the Bradford method. The protein concentration of the supernatant was calculated on the basis of a calibration curve with bovine 7-globulin as standard protein using Quick Start Protein Assay (BioRad) based on the Bradford method, and the protein concentration was defined as an amount of protein produced. FIG. 3 shows relative amount of protein produced on day 3 and day 4 of culture in Example 1 and Comparative Examples 1 and 2 against the amount of protein produced on day 4 of culture in Comparative Example 1, which is defined as 100%. In Example 1, the productivity was higher than that in Comparative Example 1 on both day 3 and day 4 of culture. In Comparative Example 2, the productivity was lower than that in Comparative Example 1. This fact revealed that when a mixture of glucose and ammonia was fed, the protein productivity was improved as compared to a case where glucose was not fed, or glucose and ammonia were separately fed in the same amount. Further, comparison with Comparative Example 2 indicated that it was important to mix glucose and ammonia before feeding.

Example 2

Using *Trichoderma reesei* X3AB1 strain, a protein containing a cellulase was produced in the same manner as in Example 1. The cells were precultured for 2 days in the same manner as in Example 1, followed by performing main culture. The initial culture medium used in the main culture was identical to that in Example 1. A preculture solution was inoculated in an amount of 10% (v/v %) in a 250 mL-volume jar fermenter BJR-25NA1S-8M (Biott) containing 100 mL of the initial culture medium. The setting of the jar fermenter was the same as in Example 1. Glucose was dissolved in a 10% ammonia aqueous solution, and the solution was appropriately diluted to prepare mixtures of various concentrations of glucose and ammonia. The prepared mixtures of glucose and ammonia were as follows and the mixtures had a pH of 10.9 or more and 11.9 or less: 5% ammonia/2.5% glucose aqueous solution (hereinafter, referred to as 5N2.5G), 5% ammonia/5% glucose aqueous solution (hereinafter, referred to as 5N5G), 5% ammonia/10% glucose aqueous solution (hereinafter, referred to as 5N10G), 5% ammonia/20% glucose aqueous solution (hereinafter, referred to as 5N20G), 5% ammonia/30% glucose aqueous solution (hereinafter, referred to as 5N30G), 5% ammonia/40% glucose aqueous solution (hereinafter, referred to as 5N40G) and 5% ammonia/50% glucose aqueous solution (hereinafter, referred to as 5N50G). These mixtures of glucose and ammonia were appropriately fed to the culture solution during culture. The amount of the mixture of glucose and ammonia fed was controlled so that the pH of the culture solution was maintained within the above-described predetermined range. The culture was ended at the time when the pH of the culture solution exceeded 5.5.

Comparative Example 3

A microorganism was cultured in the same manner as in Example 2 except that instead of the mixture of glucose and ammonia, a 5% ammonia aqueous solution was fed.

Test 4: Amount of Protein Produced

The protein concentration in the supernatant from the culture at the end of culture, which had been obtained in each of Examples 2 and Comparative Example 3 was measured by a Bradford method as in Test 3. FIG. 4 shows a relative amount of protein produced in Example 2 against the amount of protein produced in Comparative Example 3, which is defined as 100%. In Example 2, the productivity was higher than that in Comparative Example 3 in culture using a mixture of any concentration of glucose and ammonia.

FIG. 5 shows a time-dependent change in the hourly amount of glucose fed in culture using 5N2.5G in Example 2. The hourly amount of glucose fed in culture with 5N2.5G was very small as compared to that in Example 1. The amount of protein produced per amount of the carbon source (powder cellulose and glucose) used for culturing was calculated. FIG. 6 shows a relative amount of protein produced per carbon source in Example 2 against the amount of protein produced in Comparative Example 3, which is defined as 100%. The amount of protein produced per carbon source tended to be improved at the time of using a mixture of a low concentration of glucose and ammonia, and decrease as the glucose concentration in the mixture increased. Therefore, it was indicated that improvement of protein productivity by feeding of the mixture of glucose and ammonia resulted from improvement of the amount of protein produced per carbon source.

The above results reveal that feeding of the mixture of glucose and ammonia has an effect of improving not only the amount of protein produced per culture but also the amount of protein produced per carbon source used, and feeding of the mixture is effective even when glucose is fed in a very small amount of 0.1 g/L/hr or less.

What is claimed is:

1. A method for producing protein, comprising culturing a microorganism while feeding a mixture of glucose and ammonia, wherein, in the mixture, glucose and ammonia are present at a mass ratio of from 0.5 to 10:1.

2. The method according to claim 1, wherein the culturing is performed in the presence of at least one selected from the group consisting of cellulose and cellobiose.

3. The method according to claim 2, wherein the microorganism contains a cellulose-inducing promoter or a cellobiose-inducing promoter.

4. The method according to claim 3, wherein a gene encoding the protein is linked downstream of the promoter.

5. The method according to claim 4, wherein the promoter is a cellulase gene promoter of a filamentous fungus, and the protein is an enzyme.

6. The method according to claim 5, wherein the protein is a cellulase.

7. The method according to claim 1, wherein the mixture is fed in an amount of 8 g/hr or less per L of an initial culture medium in terms of the amount of glucose added to the mixture.

8. The method according to claim 1, wherein the pH of a culture is adjusted to from 3 to 7 by feeding the mixture.

9. The method according to claim 1, wherein the mixture contains glucose in an amount of from 2 to 90 g per 100 mL.

10. The method according to claim 1, wherein the mixture is alkaline at 25° C.

11. The method according to claim 1, wherein the microorganism is a filamentous fungus.

12. The method according to claim 11, wherein the filamentous fungus is a *Trichoderma* fungus.

13. The method according to claim 12, wherein the *Trichoderma* fungus is *Trichoderma reesei*.

14. The method according to claim 2, wherein the protein is an enzyme involved in biomass degradation or biomass saccharification.

15. The method according to claim 2, wherein the total concentration of cellulose or cellobiose in a culture of the microorganism is from 1 to 15 mass/vol %.

16. The method according to claim 1, further comprising collecting the protein from a culture of the microorganism.

* * * * *

SEQUENCE LISTING

<160> NUMBER OF SEQ ID NOS: 3

<210> SEQ ID NO 1
<211> LENGTH: 1640
<212> TYPE: DNA
<213> ORGANISM: Trichoderma reesei
<220> FEATURE:
<223> OTHER INFORMATION: cbh1 promoter

<400> SEQUENCE: 1

| | | | | | |
|---|---|---|---|---|---|
| tgcaaagttt | tgtttcggct | acggtgaaga | actggatact | tgttgtgtct | tctgtgtatt | 60 |
| tttgtggcaa | caagaggcca | gagacaatct | attcaaacac | caagcttgct | cttttgagct | 120 |
| acaagaacct | gtggggtata | tatctagagt | tgtgaagtcg | gtaatcccgc | tgtatagtaa | 180 |
| tacgagtcgc | atctaaatac | tccgaagctg | ctgcgaaccc | ggagaatcga | gatgtgctgg | 240 |
| aaagcttcta | gcgagcggct | aaattagcat | gaaaggctat | gagaaattct | ggagacggct | 300 |
| tgttgaatca | tggcgttcca | ttcttcgaca | agcaaagcgt | tccgtcgcag | tagcaggcac | 360 |
| tcattcccga | aaaaactcgg | agattcctaa | gtagcgatgg | aaccggaata | atataatagg | 420 |
| caatacattg | agttgcctcg | acggttgcaa | tgcaggggta | ctgagcttgg | acataactgt | 480 |
| tccgtacccc | acctcttctc | aacctttggc | gtttccctga | ttcagcgtac | ccgtacaagt | 540 |
| cgtaatcact | attaacccag | actgaccgga | cgtgttttgc | ccttcatttg | gagaaataat | 600 |
| gtcattgcga | tgtgtaattt | gcctgcttga | ccgactgggg | ctgttcgaag | cccgaatgta | 660 |
| ggattgttat | ccgaactctg | ctcgtagagg | catgttgtga | atctgtgtcg | ggcaggacac | 720 |
| gcctcgaagg | ttcacggcaa | gggaaaccac | cgatagcagt | gtctagtagc | aacctgtaaa | 780 |
| gccgcaatgc | agcatcactg | gaaaatacaa | accaatggct | aaaagtacat | aagttaatgc | 840 |
| ctaaagaagt | catataccag | cggctaataa | ttgtacaatc | aagtggctaa | acgtaccgta | 900 |
| atttgccaac | ggcttgtggg | gttgcagaag | caacggcaaa | gccccacttc | cccacgtttg | 960 |
| tttcttcact | cagtccaatc | tcagctggtg | atccccaat | tgggtcgctt | gtttgttccg | 1020 |
| gtgaagtgaa | agaagacaga | ggtaagaatg | tctgactcgg | agcgttttgc | atacaaccaa | 1080 |
| gggcagtgat | ggaagacagt | gaaatgttga | cattcaagga | gtatttagcc | agggatgctt | 1140 |
| gagtgtatcg | tgtaaggagg | tttgtctgcc | gatacgacga | atactgtata | gtcacttctg | 1200 |
| atgaagtggt | ccatattgaa | atgtaagtcg | gcactgaaca | ggcaaaagat | tgagttgaaa | 1260 |
| ctgcctaaga | tctcgggccc | tcgggccttc | ggcctttggg | tgtacatgtt | tgtgctccgg | 1320 |
| gcaaatgcaa | agtgtggtag | gatcgaacac | actgctgcct | ttaccaagca | gctgagggta | 1380 |
| tgtgataggc | aaatgttcag | gggccactgc | atggtttcga | atagaaagag | aagcttagcc | 1440 |
| aagaacaata | gccgataaag | atagcctcat | taaacggaat | gagctagtag | gcaaagtcag | 1500 |
| cgaatgtgta | tatataaagg | ttcgaggtcc | gtgcctccct | catgctctcc | ccatctactc | 1560 |
| atcaactcag | atcctccagg | agacttgtac | accatctttt | gaggcacaga | aacccaatag | 1620 |
| tcaaccgcgg | actgcgcatc | | | | | 1640 |

<210> SEQ ID NO 2
<211> LENGTH: 1477
<212> TYPE: DNA
<213> ORGANISM: Trichoderma reesei
<220> FEATURE:
<223> OTHER INFORMATION: egl1 promoter

<400> SEQUENCE: 2

| | | | | | |
|---|---|---|---|---|---|
| tttcagcaat | gcgtggcgtt | ggcaggcgac | ttcgcggcag | tgcatgagcg | atattcgggg | 60 |

```
tcgttgaagc cgacgttcac gccggagatt ggcatgatcc cagtgcttta catcatcggg      120
gccaaatgcc ggcatcctgt tgtgcggcgg gaggccttgg gtcttttgag gcggcaaccg      180
atccgggagg cggtttggga tagcgttgtt gttgccaggg tagtggagag gataatggag      240
attgaggagg ttgggtttga gaagtgggaa atgatacaga gtatggaaca ggttccggtg      300
tggcagaggg ttgagacgct gtcttgggca catgtcgtcg tcgatggaca gtctgcgggc      360
agagtggaca ttaactatac gttctgcgcg cgagagggat cgcatattga gtctttcatg      420
atgtaataag cttgggcttg acagcgttct attgccagtg tatcaacgaa gtggtatgta      480
ccatcgtgct ctgtccagac gttttggtca ggtcgacaaa caggcttttc ttcctattct      540
ctttctttga tatatacacg cttagaaatg tgtcaaaaag aacagaaacc tcttttgatg      600
tagttatgcg catgctagac tgctcctgtt tcatgtggtt acaacaaaca gtctgatcga      660
cttcgaatac ttggactgat gaaggttgta cagattgctg acagatgtcg taatgcagag      720
caaggctgta gattccataa aaccagttgc ttcgcctgct gtggctctgg agaaccaaag      780
agacgtgtct cgggagggta agtggtatcg aatctatgag agaagcccag tctaagagag      840
gaccatctcg ccaggggaag atgaagctgg ttacaactga tttgttttcc cgtctgccac      900
catggtatag agcctggacc aatcaggcta aatcattgta taataaagc ctagagaaaa      960 cctgaaatct gtcctcgtcc tttgtccgtt gtctaattat ccgttatttt cgaacgatga     1020
tacagtatga gttttgccga aattttgcta aaggtactat cgacggggga cacaagggtt     1080
gagtctgtat aacggctcga aacagcagct ggtagcagga atccaggccc gcgtttcatt     1140
tggattcatt ttcccatatt ccccttgcag aaggatacga cagtagcatt ggaaaccgta     1200
aatgacggca aaaagcatgg ttctgctcag atactccaag ccaacctatc gggtcctgga     1260
ggctatttcc aacatctcat agcctaacag aaataacgga agtcggcatc tgtatcgctc     1320
aaactgacca gacgagcccg ccatatcgag gcagagttac tctgtgttgc aaatccaact     1380
tataaagaca acaaccgcaa actttgtctt gtcgccatca gattgttcgc caagcaccct     1440
cccccccccc tatcttagtc cttcttgttg tcccaaa                              1477
```

<210> SEQ ID NO 3
<211> LENGTH: 1084
<212> TYPE: DNA
<213> ORGANISM: Trichoderma reesei
<220> FEATURE:
<223> OTHER INFORMATION: xyn3 promoter

<400> SEQUENCE: 3

```
gggaattccg tgattgacaa aatctattcg tatcaaacgt tcatgccgcc gtctccagtc       60
tcctcacgct atggtgcttg atatacataa ggggggggacg ttgaatatat gttcccagtt      120
tacctccaca taagaaatat ctcctttgga cggtctctgc aattttgccc tcaagactct      180
gcagacaatc cctctgtgct ttaaaacccc cgagtatccc ggtcacctga tggcgcaagt      240
ctcaacttcc ccaggatgcc gtctcctcat ctccgtgatg gtaacaaccg catataaggg      300
acttttgtct tctttaggct tcggacgagg gggttctttc ccagatcaat gccttgaccg      360
aaactgtcaa gatggctata taggacactg tcaattttgc catttcagtc cgggtattta      420
gacttaaaag cacctagtat ttatggttaa taaatctccg ggcaaaggtc tctttccgtg      480
cgtgtctgat gggttatgct aagctcatct ccgcagacag ggtagtaaca gaggtagccg      540
ttccttggaa agacggttaa ttgacttctt gactttgact gtccaattcg catggctaat      600
```

```
tgcggcaaaa atgatgccat atggccccgt gggcacaact ttctcacaag tctctggtgt      660
cttgactgag gtcgatgttg tgctctttct tcccaactat acaagtctaa actcctcagt      720
aaatcgatac aaggtaaatt taaactctct ggttactctt cctaccaaaa ggccctggtt      780
acatttcgtg tatacccgag gcggctgaat ctgggggact cacataggtg gatgcaatgt      840
gctattagcc agctacgcat atacaatcaa acattgaaaa tcaaaggata tacaacaact      900
ttgacgattt tccataaatt ggcatcatct ttctgagtcc tgatggatgt cagacagcaa      960
gcggacaagc tggctcatga ctcaatcctc cgaatacatc gcatcatcta ggagccattc     1020
tcacctcgaa acttctacca tctttccact gagtttcaat tgaggcggac accatggaag     1080
cacc                                                                  1084
```